(12) United States Patent
Spowart et al.

(10) Patent No.: US 7,317,964 B1
(45) Date of Patent: *Jan. 8, 2008

(54) HIGH SPEED AND REPEATABILITY SERIAL SECTIONING METHOD FOR 3-D RECONSTRUCTION OF MICROSTRUCTURES

(75) Inventors: Jonathan E. Spowart, Bellbrook, OH (US); Herbert M. Mullens, Huber Heights, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 135 days.

This patent is subject to a terminal disclaimer.

(21) Appl. No.: 11/083,920

(22) Filed: Mar. 21, 2005

Related U.S. Application Data

(63) Continuation-in-part of application No. 10/409,708, filed on Apr. 4, 2003, now abandoned.

(51) Int. Cl.
*G06F 19/00* (2006.01)
(52) U.S. Cl. .................. 700/182; 700/98; 700/118; 700/159
(58) Field of Classification Search .............. 700/97, 700/98, 117, 118, 182, 159, 119, 120; 433/17, 433/201.1; 106/35; 51/307, 308, 309; 438/50, 438/455; 703/1; 451/125
See application file for complete search history.

(56) References Cited

U.S. PATENT DOCUMENTS

| | | | |
|---|---|---|---|
| 6,352,406 B1 | 3/2002 | Clare et al. | |
| 6,454,811 B1 | 9/2002 | Sherwood et al. | |
| 6,485,413 B1 | 11/2002 | Boppart et al. | |
| 6,664,126 B1 * | 12/2003 | Devoe et al. | 438/50 |
| 6,884,742 B2 * | 4/2005 | Katsuda et al. | 501/98.4 |
| 6,984,261 B2 * | 1/2006 | Cummings et al. | 433/201.1 |
| 2002/0081015 A1 * | 6/2002 | Alkemper et al. | 382/141 |
| 2003/0110707 A1 * | 6/2003 | Rosenflanz et al. | 51/307 |

OTHER PUBLICATIONS

Spowart, Mullens and Puchala, "Collecting and Analyzing Microstructures in Three Dimensions: A Fully Aumated Approach", Oct. 2003, TMS, http://www.tms.org/pubs/journals/JOM/0310/Spowart/Spowart-0310.html.*

* cited by examiner

*Primary Examiner*—Leo Picard
*Assistant Examiner*—Charles Kasenge
(74) *Attorney, Agent, or Firm*—AFMCLO/JAZ; Gina S. Tollefson

(57) ABSTRACT

A high speed, high precision, high repeatability serial sectioning method for 3-D reconstruction of microstructure specimens is disclosed. The invention employs high-precision motorized metallographic polishing, viewing and computer controlled digital imaging of microstructure sections of a pre-selected pattern for 3-D microstructure reconstruction. The microstructure specimens are transferred throughout by a robotic manipulator arm providing greater precision and speed and serial-sectioning process control software provides control. The 3-D reconstruction of the invention can be analyzed in real time and can be accomplished in a matter of hours.

17 Claims, 3 Drawing Sheets

HIGH SPEED AND REPEATABILITY SERIAL SECTIONING METHOD FOR 3-D RECONSTRUCTION OF MICROSTRUCTURES

CROSS-REFERENCE TO RELATED APPLICATION

This is a continuation-in-part of application Ser. No. 10/409,708, filed Apr. 4, 2003 now abandoned, and is related to three additional co-pending CIP patent applications, all by the same inventors as the present application, titled "High Speed And Repeatability Serial Sectioning Device For 3-D Reconstruction Of Microstructures", titled "High Speed And Repeatability Serial Sectioning Method For 3-D Reconstruction Of Microstructures Using Scanning Electron Microscope", and titled "High Speed And Repeatability Serial Sectioning Method For 3-D Reconstruction Of Microstructures Using Optical Microscopy".

RIGHTS OF THE GOVERNMENT

The invention described herein may be manufactured and used by or for the Government of the United States for all governmental purposes without the payment of any royalty.

BACKGROUND OF THE INVENTION

Repeated sectioning of a material specimen on closely spaced parallel planes (commonly known as serial sectioning) is an established destructive technique for obtaining the 3-dimensional microstructure of a material specimen. Until now, the metallographic polishing techniques necessary to accomplish this task have been carried out manually, which is a time-consuming and technically high-risk process.

Existing methods for 3-D reconstruction of microstructures using serial sectioning rely on manual preparation of the sections, using a manual polishing machine and tripod polishing fixture. Hardness marking indents or other fiducial markings are used to measure the amount of material removed, and hence the thickness of the section. Once the required thickness is removed from the specimen, the specimen is then prepared for microscopy (electron or optical) and an image is taken of the surface. If large fields of view are required, many overlapping micrographs have to be taken and painstakingly reconstructed. This process is repeated for as many sections as are required. Estimates for the time taken to acquire each section range from 4 to 8 hours of skilled manual work, translating to many weeks and months of effort for any reasonable number of sections (between 50 and 100).

Other methods of serial sectioning include automatic micro-milling units that use precision diamond cutters, and also microtomes with glass or diamond blades, which can remove thin layers of material from the specimen. Although rapid, these methods have the disadvantage that only a limited number of different materials systems can be sectioned successfully using these techniques, and still produce a surface that is suitable for microscopic imaging.

In all of the current techniques, the measurement of distance between subsequent sections, plus the in-plane alignment between them is key in reconstructing the 3-D microstructure of the specimen. This means the painstaking repeated placement of fiducial markings on the constantly receding polished surface, and the measurement of the changes in their geometry, as sections are obtained. This is a highly time-consuming process and prone to error.

The invention described herein is an automatic method that accomplishes the same task as manual serial sectioning, but with a higher precision and repeatability, and a 100× increase in speed. This increase in speed is enabling in materials science research because it allows the 3-D reconstruction of material microstructures in a matter of hours, rather than the many weeks and months it currently takes. It is also enabling in a materials production environment, as 3-D microstructural data can be analyzed in real-time and the results applied toward optimizing the process, again in real time.

SUMMARY OF THE INVENTION

A high speed, high precision, high repeatability serial sectioning method for 3-D reconstruction of microstructure specimens. The invention employs high-precision motorized metallographic polishing, a microscope for viewing and computer controlled digital imaging of microstructure sections of a pre-selected pattern for 3-D microstructure reconstruction. The microstructure specimens are transferred throughout by a robotic manipulator arm, which provides greater precision and speed and serial-sectioning process control software provides control. The 3-D reconstruction of the invention can be analyzed in real time and can be accomplished in a matter of hours.

It is therefore an object of the invention to provide a high precision and repeatability serial sectioning method for 3-D reconstruction of microstructures.

It is another object of the invention to provide a high precision and repeatability serial sectioning method for 3-D construction of microstructures using motorized metallographic polishing, an optical microscope for viewing and computer controlled digital imaging.

It is another object of the invention to provide a method where automatic serial sectioning for 3-D reconstruction of microstructures can occur in a matter of hours.

It is another object of the invention to provide an automatic serial sectioning method where 3-D reconstruction of microstructures can be analyzed in real time.

These and other objects of the invention are described in the description, claims and accompanying drawings and are achieved by a high speed, high precision, high repeatability method for 3-D reconstruction of microstructure specimens comprising the steps of:

polishing selected microstructure sections of said microstructure specimen using a high-precision motorized metallographic polishing unit, preparing said microstructure specimen from said polishing step for microscopic viewing and imaging;

microscopic viewing of said microstructure specimen from said preparing step;

digital imaging of said microstructure specimen for 3-D microstructure specimen reconstruction using 3-D microstructure volume rendering software providing real-time 3-D microstructure software data of said microstructure specimen;

manipulating said microstructure specimen through said polishing, preparing, viewing and imaging steps using a robotic manipulator arm;

controlling said polishing, preparing, viewing and imaging steps using serial-sectioning process control software including selecting the number of microstructure sections acquired from said microstructure specimen; and repeating said polishing, preparing and viewing and imaging steps until a pre selected number of microstructure sections from said microstructure specimen have been acquired.

DETAILED DESCRIPTION OF THE INVENTION

Figure 1:
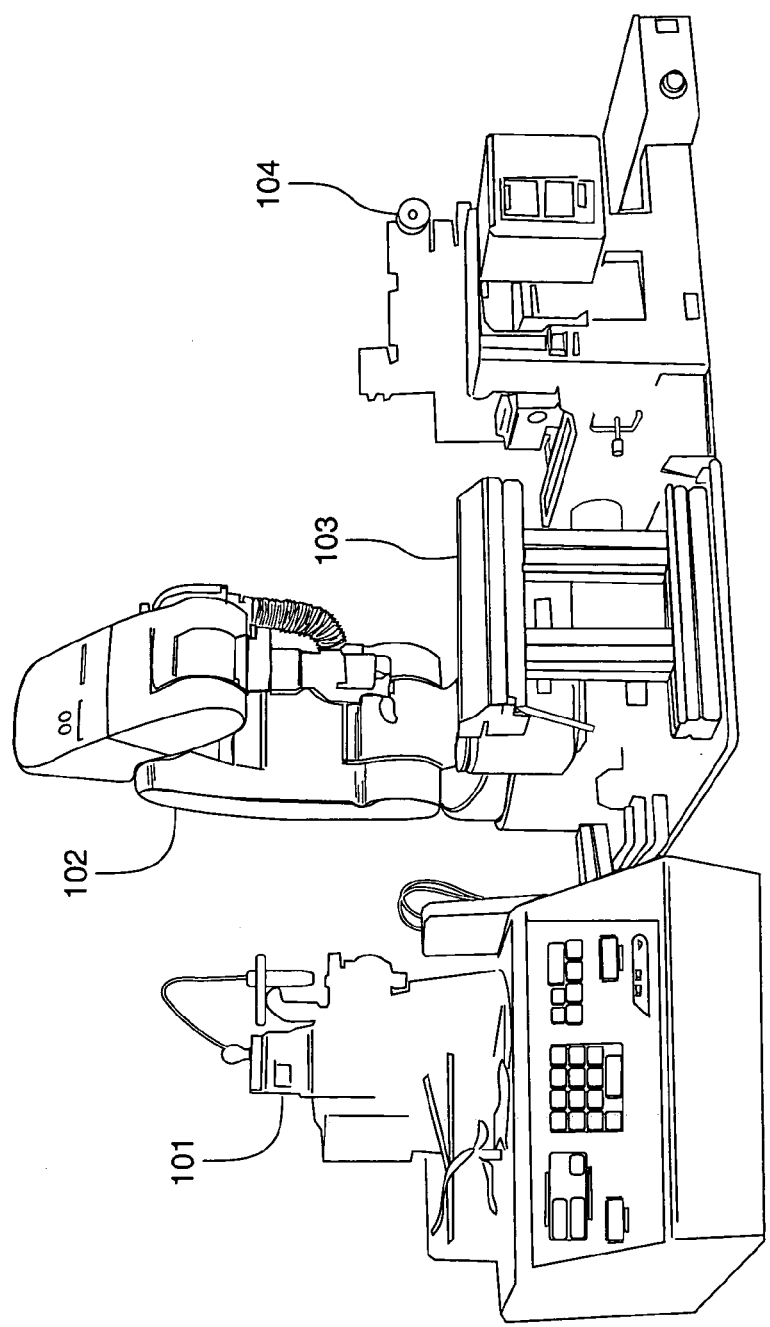
FIG. 1 shows a layout of the components of the automatic serial sectioning method of the invention.

The high speed, high precision, high repeatability serial sectioning method of the invention comprises six major steps, in a preferred arrangement, as shown in FIG. 1 and is collectively known as "Robo-Met.3D." The method includes high-precision motorized metallographic polishing, illustrated at 101, a robotic manipulating arm shown at 102, a step or preparing specimens for viewing, illustrated at 103, an optical microscope for specimen viewing shown at 104, and a PC workstation running the serial-sectioning process control software ("Robo_control.vi") and 3-D microstructure volume rendering software ("Robo-Met_render"), both included in Appendix A.

The 3-D reconstruction of a desired microstructure specimen is accomplished by acquiring a selected number of section planes of said specimen. For purposes of this application, the terms "section plane" and "section" are synonymous, each being defined as a 2-dimensional plane which passes through a 3-dimensional object. Each section plane is obtained by removing a prescribed depth of material from the surface of the 3-dimensional object, and then imaging the newly-revealed surface. The section "thickness" or section "depth" is defined as the linear distance between adjacent sectioning planes, measured along their normal planes. The section planes are polished, viewed and imaged from differing perspectives. Each microstructure section is generated by the metallographic polishing of a material specimen, using the high-precision motorized metallographic polishing unit 101. The polishing action produces sections of the specimen by removing a thin layer of material from the specimen, while keeping the new specimen surface flat, parallel and free from scratches and other surface defects such that it can be imaged using an optical microscope in reflective mode.

Figure 3:
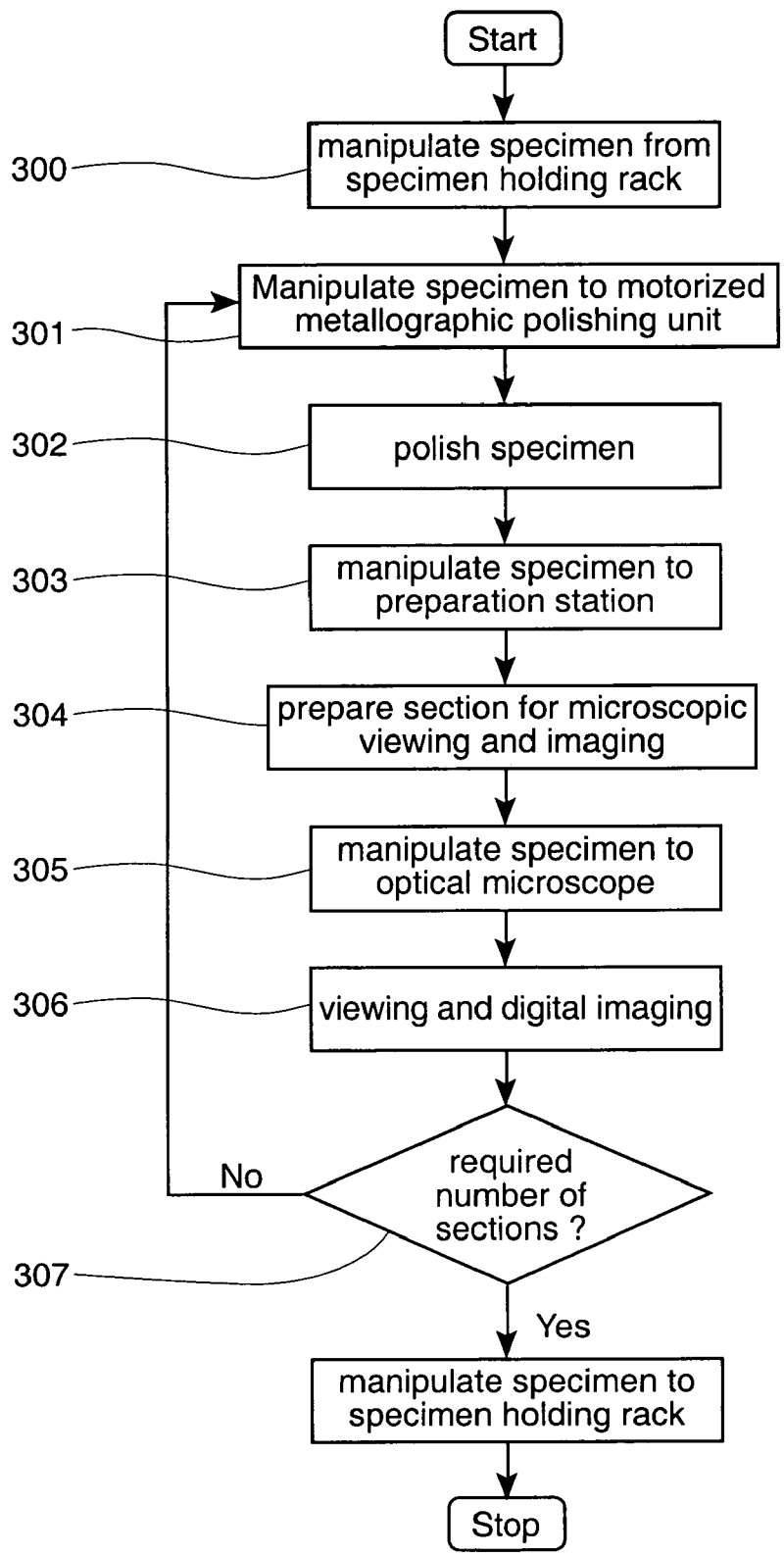
FIG. 3 is a flow diagram illustrating the functioning of the serial-sectioning process control software according to the method of the invention.

The robotic arm 102 is used for transferring the specimens from a specimen rack to the polishing unit, where it is held securely for polishing. FIG. 3 illustrates a flow diagram illustrating the functioning of the serial-sectioning process control software according to the method of the invention. The step of manipulating the specimen to a motorized metallic polishing unit in the Robo_control.vi software is illustrated at 301 in FIG. 3.

The polishing unit comprises an extremely flat platen covered by a diamond-impregnated polishing film. The diamond polishing film may be replaced by a slurry of abrasive powder in a lubricant base, either with or without a polishing cloth or pad between the polishing platen and the specimen.

The flat platen rotates at a fixed rate of revolutions per minute with the specimen held against the polishing surface with a controlled amount of force, for a controlled amount of time, as specified by the user in the control program Robo-control.vi, and illustrated at step 301 in FIG. 3. Different materials require different amounts of polishing because of differences in hardness. For example, a soft metal alloy may require a shorter amount of time to remove the same depth of material as a hard metal alloy would, and/or require more or less force during polishing, depending on the material. A relatively soft material containing hard phases (e.g. a composite material) may also require longer polishing times, and/or greater amounts of force during polishing, and may require different amounts of lubricant than a softer material.

In an alternative arrangement of the invention, instead of the specimen being transferred to the polishing unit where it is held securely for polishing, the specimen is held directly against the polishing film by the robot arm. The robot is responsible for moving the specimen on the film, which is rotating underneath it, and controlling the amount of downward force applied to the specimen during polishing. This obviates the need for a separate specimen carrier on the polishing machine itself.

A lubricant is applied to the polishing film to prevent scratching of the specimen surface. A wiping cloth is employed to prevent the material removed by the polishing action from re-contaminating the specimen as the film rotates. This step of preparing the specimen for microscopic viewing and imaging is illustrated at 304 in the flow diagram of FIG. 3. It is important to keep the specimen surface as clean as possible because contaminants tend to scratch or pit the surface, reducing the quality of, and introducing artifacts in the microstructure sections obtained via microscopy.

In another arrangement of the invention, one or more additional polishing machines are employed for either "fine polishing" or "rough polishing" the specimen surface in addition to the main polishing machine, and to adjust either the surface finish or the amount of material removal per sectioning step, using either diamond polishing films or an alternative polishing medium. A "fine polishing" is useful when the amount of material being removed in each polishing step is small, and around the same depth as the fine polishing will provide during surface preparation for optical microscopy. A "rough polishing" is used when the amount of material being removed in each polishing step is larger than the depth of the fine polishing. Therefore, the rough polishing must be followed by a subsequent fine polishing to prepare the specimen surface for optical microscopy, with negligible additional depth change. In some cases, the additional material removed during fine polishing can also be factored into the rough polishing step, if it is significant.

The specimen is then removed from the polishing machine using the robotic manipulator arm 102 and transferred to the specimen preparation station 103 where it is washed using an ultrasonic cleaner and dried using a stream of compressed nitrogen gas. This step in the Robo_control.vi software of manipulating the specimen to the specimen preparation station is illustrated at 303 in FIG. 3. Many other types of chemical etching, electrolytic etching, cleansing and drying agents can be used at this stage of the process, depending on the type of material. For example a Ni-based super-alloy specimen has been serial sectioned using this device, incorporating a complex washing/etching/drying routine. The routine includes ultrasonic cleaning in distilled water, followed by rinsing in isopropyl alcohol followed by drying using a stream of compressed nitrogen gas followed by 5 seconds of dip-etching in a solution comprising 5 parts water, 2 parts hydrofluoric acid, 1 part nitric acid, and 2 parts sulfuric acid, followed by 10 seconds of neutralizing in a saturated solution of sodium hydroxide, followed by ultrasonic cleaning in distilled water followed by rinsing in isopropyl alcohol, followed by drying using a stream of compressed nitrogen gas. Other materials may require different etching/cleaning/drying procedures, including electrolytic etching rather than chemical etching as in this case.

Using automatic washing, etching and drying steps is an improvement over the prior art because it allows a very high degree of control over these steps, which gives excellent repeatability, and also allows completely autonomous operation since the material specimen is not removed from the device in order to do this manually. It also makes the process quicker than using a manual process.

The specimen is then moved to the microscope stage 104 where it is positioned over the objective, and automatically focused by computer control. This step in the Robo_control.vi software of manipulating the specimen to the optical microscope is illustrated at 305 in FIG. 3. The objective refers to the final lens in the microscope light path, and can be one of a number of lenses used to obtain images at different magnifications, commonly mounted in a rotating nosepiece either with or without computer control to select different objective lenses. In the present arrangement of the invention, an optical microscope is used, however, an optical microscope may be replaced with a scanning electron microscope (SEM), either imaging in secondary electron mode or backscattered electron mode. This alternative arrangement requires an additional transfer stage between the specimen preparation environment and the vacuum environment of the SEM, possibly using an air-lock mechanism. The benefit of using a scanning electron microscope is that higher magnifications and/or higher resolution images may be captured to build the 3-D microstructural representation. In addition, alternative contrast mechanisms operate in the scanning electron microscope, such as contrast from the different atomic species in the specimen, which would not necessarily be visible in the optical microscope. In addition, more chemical information can be obtained from the x-rays than are emitted due to interaction with the electron beam. This would allow for Energy-Dispersive Spectroscopy to be used to map out regions of similar chemical nature on the specimen surface, and allowing 3-D chemical mapping in the reconstructed microstructure. Further, Electron Back-Scattered Diffraction contrast can be used to obtain crystallographic information from the 2-D sections, including the crystallographic orientations of different regions of the material, via Orientation-Imaging Microscopy (OIM). This will allow for 3-D crystallographic mapping of the reconstructed microstructure.

In another possible arrangement of the invention, there is a real-time Laue x-ray camera attached to the device, which allows for point-by-point mapping of the crystallographic orientations of the different regions of the material. This is an alternative method for obtaining 3-D crystallographic mapping of the reconstructed microstructure, without resorting to the use of a scanning electron microscope. This is an advantage, since it obviates the need for an additional transfer stage between the specimen preparation environment and the vacuum environment of the scanning electron microscope.

By controlling the x-y position of the microstructure section at the microscope stage, bright-field optical micrographic images of the newly polished specimen surface are taken using a computer-controlled digital camera in a prespecified pattern. The entire surface, or specific regions near the edges of the specimen are imaged, in order that a novel Three-Plane Polishing (TPP) technique, an additional embodiment of the invention, can be used to reconstruct a 3-D microstructure. The entire surface is imaged when the specimen is small, and/or the regions of interest extend over the entire specimen surface. Specific regions near the edges of the specimen are imaged when the region of interest does not extend over the majority of the specimen, and so the (larger file size) image of the entire surface would add no additional microstructural information. In addition to bright-field optical micrographic images, imaging techniques that may be used to create the 2-D sections are dark-field optical microscopy, polarized-light optical microscopy, Differential Interference Contrast microscopy, and confocal laser microscopy. Dark-field microscopy is used to identify regions of the microstructure that are strongly diffracting in comparison with the majority of the specimen, and thus allows the investigation of precipitates, abnormal grains and other defects in the microstructure. Polarized light microscopy is used to examine the optical properties of the specimen, using a polarizer filter and a rotating analyzer filter. Optically active specimens such as birefringent materials will show different contrast than optically inactive materials under polarized light. This can be used to reveal the optic and/or crystallographic axes in the specimen and gain information regarding the crystalline orientations in 2-D and 3-D once the microstructure has been reconstructed. One drawback of this technique is that only optically active materials will show this effect. Differential Interference Contrast microscopy is used to reveal surface relief on the polished specimen. It will show contrast whenever there is a change in height between different regions on the surface, and can be used to delineate features resulting from differential chemical or electrochemical etching, or from differential mechanical polishing action on phases within the same material that have different mechanical properties, e.g. high or low hardness. However, this contrast mechanism is very sensitive to surface scratches and other defects from polishing, thereby making precise control of the polishing steps of key importance. Confocal laser microscopy can also be used to obtain contrast from different height regions on the specimen surface, as an alternative to Differential Interference Contrast microscopy. It has the advantage that only the parts of the specimen surface that are in focus will be imaged, so that a very sharp, high-resolution image can be created where bright-field microscopy would give a blurred image. In addition, height differences that might arise from differential chemical or electrochemical etching, or from differential mechanical polishing action on phases within the same material that have different mechanical properties can be accurately measured by this technique and used to identify different microstructural features. One disadvantage of this technique is that it requires specialized equipment (i.e., a laser scanning confocal microscope, rather than a light microscope).

In an alternative arrangement of the invention, instead of the specimen being transferred to the microscope stage, where it is held securely for micrographic imaging, the specimen is held directly above the microscope objective. The robot is responsible for focusing the microscope (by moving the specimen vertically) and also for aligning the specimen in the x-y (horizontal) plane. Under Robo_control.vi software computer control, the specimen is translated and/or rotated in the x-y plane to obtain multiple images of the newly polished surface, possibly with direct reference to the previously imaged surfaces. Continuous slow traversal of the specimen above the objective, coupled with continuous image capturing by the computer (i.e. digital video) will obviate the need for "image stitching" of the collected images.

In the present arrangement of the invention, the microscope uses image "stitching" software routine to automatically create large images from multiple overlapping fields of view. If a region of interest (ROI) has been specified in the microstructure, then the sections pertaining to the ROI will be displayed on the computer monitor, via the Robo-Met_render program, running on the PC workstation. This allows real-time 3-D microstructural data to be displayed as the serial sectioning continues. Once the micrographic images have been captured, the specimen is returned to the polishing machine 101 and a new section is polished from the specimen surface. This process repeats until the desired number of sections have been acquired, as specified by the user in the process control software ("Robo-control.vi") and illustrated at 307 in FIG. 3 which is also running on the PC workstation.

Figure 2:
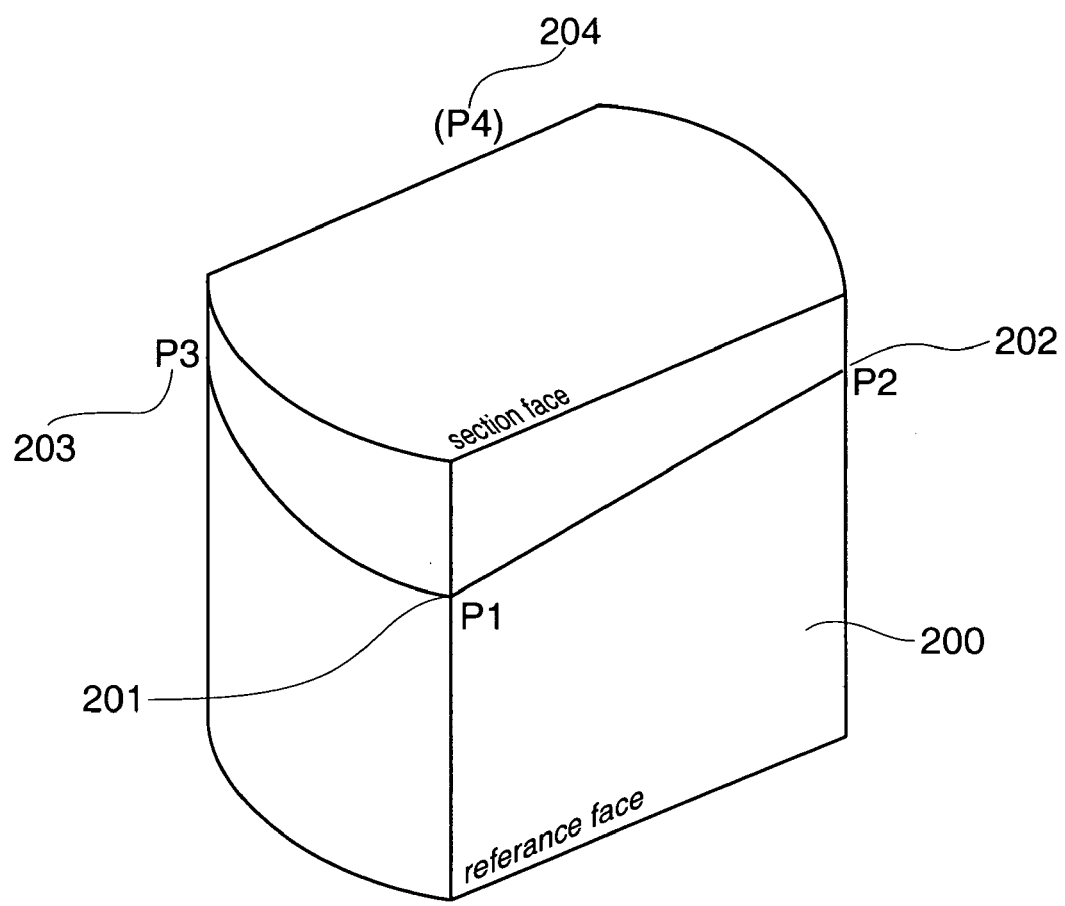
FIG. 2 shows a diagram of three-plane polishing according to the method of the invention.

The Three-Plane Polishing procedure obviates both the need to measure the (vertical) distance between subsequent microstructure sections of the material specimen, and the correlation routines required to align subsequent layers in the (horizontal) plane. The technique relies on metallographically polishing and then micrographically imaging the sides of the specimen (the "reference faces") prior to removing any sections from the "Sectioning Face", which is perpendicular to the sides. These three planes of polish define the Three-Plane Polishing technique and are illustrated in FIG. 2. In three-plane polishing, the sectioning plane 200 is aligned by fast Fourier transform cross-correlation of edge-most pixels with reference faces. Corners of reference face 200 include P1 at 201 and P2 at 202. Corners P3 at 203 and P4 at 204 are for a reference face not shown in the figure. Only 3 out of 4 points are necessary to locate the microstructure section plane in 3-D space, thus ensuring useful redundancy in the technique. As each new section is produced, computer software compares the microstructural features on the extreme edges of the sectioning face with the corresponding features on the sectioning faces, using Fast Fourier Transform (FFT)-based cross-correlation techniques. The most likely position for the sectioning plane to exist within the 3-D volume of the specimen is ascertained by the computer program. Once the coordinates of the four points (P1, P2, P3, P4), shown at 201-204 in FIG. 2, where the section plane intercepts the reference faces, are established (only 3 are needed), a 3-D model is constructed inside the computer, with the sectioning plane in its proper place. The model is updated as each new section plane is created and located within the volume of the specimen. Small changes in the spacing, rotation, and parallelism between subsequent sections are thereby accounted for using this technique.

Since the sections are correlated with the reference faces (i.e. sides) of the specimen, rather than with each other, the 3-D microstructure reconstructed in this way is less susceptible to systematic alignment errors than those reconstructed using cross-correlation between subsequent layers, in the horizontal plane, e.g.; parallel cylindrical fibers oriented at an angle to the sectioning plane will always be reconstructed as parallel elliptical fibers, oriented perpendicular to the sectioning plane, introducing a systematic error into the reconstruction.

There are a number of distinct advantages of the invention over the current state of the art. The present invention increases the throughput of any manual serial sectioning process by approximately 100 times. In addition to this, the use of the TPP technique allows a unique and more precise positioning of the section planes in 3-D space. That is, it completely obviates the need for independently measuring the section depth (e.g. using fiducial marks) and then using cross-correlation techniques to determine the 2-D transformation (translation and/or rotation) to achieve registry between subsequent layers. Using metallographic polishing techniques allows for increased flexibility over micro-milling or microtomy techniques, with respect to the numbers of different materials systems that can be examined in 3-D. Materials that can be examined in 3-D that were previously not candidates for manual reconstruction include metal-matrix composites such as aluminum-silicon carbide and aluminum-alumina, and any other material that contains a relatively soft phase and one or more relatively hard phases. Also, some materials (e.g. steels and other iron-containing alloys) suffer chemical attack during the micro-milling process due to chemical interactions between the material and the carbon in the diamond blade typically used. In addition, the fully automatic nature of the method of the invention means that the method can collect the 3-D microstructural data unattended (i.e. overnight), thereby dramatically increasing productivity. When used in a more interactive mode, the real-time 3-D microstructural data provided by the Robo-Met_render program allows the user to change the sectioning process as it occurs, (e.g. adjusting the slice thickness, or changing the ROI) thereby giving great flexibility to the machine. The use of a robotic arm to position the specimen in the polishing machine, and to transfer the specimen between the microscope and the other stages of the process is novel, and allows not only for full automation of the machine, but also increases the accuracy of the sectioning procedure due to the very high repeatability of the robot, vs. a manual operation.

While the method herein described constitute a preferred embodiment of the invention, it is to be understood that the invention is not limited to this precise form of method and that changes may be made therein without departing from the scope of the invention, which is defined in the appended claims.

We claim:

1. A high speed, high precision, high repeatability method for 3-D reconstruction of microstructure specimens comprising the steps of:

polishing selected serial microstructure sections of said microstructure specimen using a high-precision, high speed and high repeatability motorized metallographic polishing unit, measuring vertical distance between said selected serial microstructure sections; preparing said microstructure specimen from said polishing step for microscopic viewing and imaging;

microscopic viewing of said microstructure specimen from said preparing step;

digital imaging of said microstructure specimen for 3-D microstructure specimen reconstruction using data from said measuring step and 3-D microstructure volume rendering software providing real-time 3-D microstructure software data of said microstructure specimen;

manipulating said microstructure specimen through said polishing, preparing, viewing and imaging steps using a robotic manipulator arm;

controlling said polishing, preparing, viewing and imaging steps using serial-sectioning process control software including selecting the number of microstructure sections acquired from said microstructure specimen; and repeating said polishing, preparing and viewing and imaging steps until a pre selected number of microstructure sections from said microstructure specimen have been acquired.

2. The high speed, high precision, high repeatability method for 3-D reconstruction of microstructure specimens of claim 1 wherein said viewing step further comprises viewing said microstructure section from said preparing step with an optical microscope.

3. The high speed, high precision, high repeatability method for 3-D reconstruction of microstructure specimens of claim 1 further comprising the step of, after said polishing step, preventing scratching and contamination of said microstructure specimen.

4. The high speed, high precision, high repeatability method for 3-D reconstruction of microstructure, specimens of claim 3 wherein said preventing step further comprises preventing scratching and contamination of said microstructure specimen by collecting material removed by said metallographic polishing unit from re-contaminating said microstructure specimen during rotation using a wiping cloth.

5. The high speed, high precision, high repeatability method for 3-D reconstruction of microstructure specimens of claim 3 wherein said preventing step further comprises preventing scratching and contamination of said microstructure specimen by applying a lubricant.

6. The high speed, high precision, high repeatability method for 30-D reconstruction of microstructure specimens of claim 1 wherein said polishing step further comprises the steps of:

computer controlled microstructure specimen rotating; and computer controlled microstructure specimen securing.

7. The high speed, high precision, high repeatability method for 3-D reconstruction of microstructure specimens of claim 1 wherein said polishing step further comprises fine polishing selected microstructure sections.

8. The high speed, high precision, high repeatability method for 3-D reconstruction of microstructure specimens of claim 1 wherein said polishing step further comprises rough polishing selected microstructure sections.

9. The high speed, high precision, high repeatability method for 3-D reconstruction of microstructure specimens of claim 1 wherein said preparing step further comprises the steps of:

automated cleaning of said microstructure specimen from said polishing step;

automated drying of said microstructure specimen from said cleaning step.

10. The high speed, high precision, high repeatability method for 3-D reconstruction of microstructure specimens of claim 9 wherein said automated cleaning step further comprises automated ultrasonic cleaning of said microstructure specimen from said polishing step.

11. The high speed, high precision, high repeatability method for 3-D reconstruction of microstructure specimens of claim 9 wherein said automated drying step further comprises automated drying using a stream of compressed nitrogen gas.

12. The high speed, high precision, high repeatability method for 3-D reconstruction of microstructure specimens of claim 1 further comprising the step of point-by-point mapping of crystallographic orientations of various regions of said polished specimen using a real-time x-ray camera.

13. The high speed, high precision, high repeatability method for 3-D reconstruction of microstructure specimens of claim 1 wherein said microscopic viewing step further comprises the step of controlling x-y planar position of said microstructure specimen.

14. The high speed, high precision, high repeatability method for 3-D reconstruction of microstructure specimens of claim 1 wherein said digital imaging step further comprises the step of controlling digital imaging in a pre-specified pattern whereby an entire surface or edges of the specimen are imaged.

15. The high speed, high precision, high repeatability method for 3-D reconstruction of microstructure specimens of claim 1 wherein said digital imaging step further comprises the step of creating large images from multiple overlapping fields of view using computer volume rendering software.

16. The high speed, high precision, high repeatability method for 3-D reconstruction of microstructure specimens of claim 1 wherein said digital imaging step further comprises the step of specifying regions-of-interest in said microstructure specimen.

17. A high speed, high precision, high repeatability serial sectioning method for 3-D reconstruction of microstructure specimens comprising the steps of:

polishing selected microstructure sections of said microstructure specimen using a three-plane polishing procedure comprising the steps of:

aligning a sectioning plane by a fast Fourier transform cross-correlation of edge-most pixels with references faces;

comparing microstructural features on extreme edges of a sectioning face with corresponding features on said reference face using fast Fourier transform based cross-correlation techniques, thereby establishing four points where section planes intercept references faces;

constructing a three-dimensional model inside a computer with sectioning plane in its proper place; and updating said three-dimensional model as each new section plane is created;

preparing of said microstructure specimen for viewing and imaging;

computer controlled, automated viewing of said microstructure specimen from said preparing step;

computer controlled digital imaging of said microstructure specimen, a combination of previous images obtained after a preselected number of polished microstructure sections resulting in 3-D microstructure reconstruction using 3-D volume rendering software providing real-time 3-D microstructure software data of said microstructure specimen;

controlling said poling, preparing, viewing and imaging steps using a PC workstation running serial-sectioning process control software including selecting a number of microstructure sections acquired from said microstructure specimen; and repeating said polishing, preparing and viewing and imaging steps until a pre selected number of microstructure sections from said microstructure specimen have been acquired.

\* \* \* \* \*